(12) United States Patent
Shribman et al.

(10) Patent No.: US 9,526,592 B2
(45) Date of Patent: Dec. 27, 2016

(54) LOCKING IMPLANT

(76) Inventors: Victor Shribman, Kiryat Ono (IL); Rodica Greenberg, Rishon LeZion (IL)

(*) Notice: Subject to any disclaimer, the term of this patent is extended or adjusted under 35 U.S.C. 154(b) by 0 days.

(21) Appl. No.: 13/393,486

(22) PCT Filed: Aug. 26, 2010

(86) PCT No.: PCT/IL2010/000699
§ 371 (c)(1),
(2), (4) Date: May 11, 2012

(87) PCT Pub. No.: WO2011/033498
PCT Pub. Date: Mar. 24, 2011

(65) Prior Publication Data
US 2012/0270181 A1    Oct. 25, 2012

Related U.S. Application Data (60) Provisional application No. 61/244,116, filed on Sep. 21, 2009.

(51) Int. Cl.
*A61C 8/00*        (2006.01)
(52) U.S. Cl.
CPC .................. *A61C 8/0033* (2013.01)
(58) Field of Classification Search
CPC ... A61C 8/0019; A61C 8/0021; A61C 8/0022; A61C 8/0024; A61C 8/0025; A61C 8/0033; A61C 2008/0046; A61C 2008/0065; A61B 17/8685; A61B 17/32075; A61B 17/320725

USPC .......... 433/172–176, 201.1, 202.1, 215, 220, 433/221; 606/313, 327; 411/32, 60.2, 18, 411/24, 69, 80.1, 80.2
See application file for complete search history.

(56) References Cited

U.S. PATENT DOCUMENTS

| | | | | |
|---|---|---|---|---|
| 1,142,618 A | * | 6/1915 | Pauley | ................ F16B 13/0808 |
| | | | | 411/345 |
| 2,685,877 A | * | 8/1954 | Dobelle | ................ A61F 2/3603 |
| | | | | 411/21 |
| 3,579,831 A | | 5/1971 | Stevens et al. | |
| 5,141,435 A | | 8/1992 | Lillard | |
| 5,197,881 A | | 3/1993 | Chalifoux | |
| 5,611,688 A | * | 3/1997 | Hanosh | ........................ 433/174 |
| 6,004,088 A | * | 12/1999 | Hunt | ................... F16B 13/0808 |
| | | | | 411/21 |
| 2013/0310883 A1 | * | 11/2013 | Levy | ................... A61B 17/7032 |
| | | | | 606/313 |
| 2014/0363787 A1 | * | 12/2014 | Tissi | .................... A61C 8/0022 |
| | | | | 433/174 |

FOREIGN PATENT DOCUMENTS

JP           11033039 A   *   2/1999   ............... A61C 8/00

OTHER PUBLICATIONS

Machine translation of JP 11033039 A.*
(Continued)

*Primary Examiner* — Yogesh Patel
(74) *Attorney, Agent, or Firm* — The IP Law Firm of Guy Levi, LLC; Guy Levi (57) ABSTRACT

The disclosure relates to an expandable dental implant assembly for supporting a prosthesis, with a shaft member, configured to engage the central bore and cause plurality of blades to extend radially from openings disposed in the body portion, anchoring the implant into the bone structure surrounding the implant.

12 Claims, 5 Drawing Sheets

(56) References Cited

OTHER PUBLICATIONS

International Search Report; International Application No. PCT/IL2010/000699; International Filing Date: Aug. 26, 2010; Date of Mailing: Jan. 12, 2011; 3 pages.
Written Opinion of the International Searching Authority; International Application No. PCT/IL2010/000699; International Filing Date: Aug. 26, 2010; Date of Mailing: Jan. 12, 2011; 5 pages.

* cited by examiner

LOCKING IMPLANT

CROSS REFERENCE TO RELATED APPLICATIONS

This application is a U.S. National Stage Application, which claims priority to International Application No. PCT/IL2010/000699, filed on Aug. 26, 2010 and U.S. Provisional Application No. 61/244,116, filed on Sep. 21, 2009, all which are incorporated herein by reference in their entirety.

BACKGROUND

1. Technical Field

The present invention relates to an expanding bone implant and, more particularly to an oral implant having radially extendable anchoring means.

2. Discussion of Related Art

Implant dentistry involves the restoration of one or more teeth in a patient's mouth using artificial components. Such artificial components typically include a dental implant and a prosthetic tooth and/or a final abutment that is secured to the dental implant. Generally, the process for restoring a tooth is carried out in three stages.

Stage I involves implanting the dental implant into the alveolar bone (i.e., jawbone or cortica) of a patient. The surgeon first accesses the alveolar bone through the patient's gum tissue and removes any remains of the tooth to be replaced. Next, the specific site in the alveolar bone where the implant will be anchored is prepared by drilling and/or reaming to accommodate the width/diameter of the dental implant to be inserted. Then, the dental implant is inserted into the hole, typically by screwing, although other techniques are known for introducing the implant in the jawbone.

After the implant is initially installed in the bone, a temporary healing cap/screw may be secured over the exposed proximal end in order to seal the internal bore of the implant. The patient's gums are then sutured over the implant to allow the implant site to heal and to allow desired osseointegration to occur. Complete osseointegration typically takes anywhere from three to ten months.

During stage II, the surgeon reaccesses the implant fixture by making an incision through the patient's gum tissues. The healing cap/screw is then removed, exposing the proximal end of the implant. Typically, an impression coping may be attached to the implant and a mold or impression is then taken of the patient's mouth to accurately record the exact position and orientation of the implant within the mouth. Stage II is typically completed by attaching to the implant a temporary healing abutment or other transmucosal component to control the healing and growth of the patient's gum tissue around the implant site. In a modified procedure, an abutment or other transmucosal component is either integrally formed with the implant or is attached to the implant during stage I. In such a procedure, stages I and II are effectively combined in to a single stage.

Stage III involves the fabrication and placement of cosmetic tooth prosthesis to the implant fixture. The plaster analogue provides laboratory technicians with a model of the patient's mouth, including the orientation of the implant fixture and/or abutment relative to the surrounding teeth. Based on this model, the technician constructs a final restoration. The final step in the restorative process is replacing the temporary healing abutment with the final abutment and attaching a final prosthesis to the final abutment.

The dental implant is typically fabricated from pure titanium or a titanium alloy. The dental implant typically includes a body portion and a collar. The body portion is configured to extend into and osseointegrate with the alveolar bone. The top surface of the collar typically lies over, under or flush with the crest of the jawbone bone. The final abutment typically lies on the top surface and extends through the soft tissue, which lies above the alveolar bone. As mentioned above, the abutment supports the final prostheses. Typically, the coronal or crown portion of the collar and the portions of the final abutment that extend through the soft tissue have machined- or polished surfaces. This is believed in the art to prevent the accumulation of plaque and calculus and facilitates cleaning.

Conventional dental implants that provide the foundation for a prosthetic tooth as described hereinabove require a substantial amount of solid bone in which to be inserted and/or installed and/or inlaid. If there is insufficient bone quantity, quality or density, for example soft osteoporotic bone, conventional implants may suffer osseointegration failure, loosen and fail.

An expandable dental implant may comprise a screw which is torqued into a jacket having multiple deformable ends that expand into the surrounding bone; as exemplified by U.S. Pat. No. 6,332,778 (Choung), the contents of which is incorporated herein by reference in their entirety. The larger diameter provided by the expanded multiple ends, may aid in locking the implant in the osteoporotic bone.

BRIEF SUMMARY

Embodiments of the present invention provide an implant assembly, more specifically, a dental implant assembly. One assembly includes a bladed dental implant assembly for securing in a jaw bone. The bladed dental implant assembly includes a body portion configured to be located within a bore in a jaw bone.

Accordingly, according to an aspect of the present invention, the body portion of the dental implant includes axially oriented central bore, at least one opening passing from the central bore through the outside surface of the body portion of the dental implant and at least one blade pivotally or flexibly connected to the body portion of the dental implant, each blade aligned with one of the openings.

In one embodiment, the term "flexibly connected" used herein means that the junction between two elements is flexible, and this purpose can be achieved in certain embodiments by using a material of a relatively low strain to form the elements, or by thinning the junction relative to the thickness of the elements in other embodiments. In other embodiments, the term "flexible connection" indicates that the junction will not be broken even when the opposite end of either of the elements does not synchronously move with the junction end.

The bladed dental implant additionally includes a shaft member configured to engage the central bore, causing the one or more blades to swivel radially outward, thereby extending outwardly from the body portion of the dental implant to secure the dental implant into the bone structure surrounding the body portion of the dental implant.

In certain embodiments of the invention, the central bore is threaded and the shaft member is reciprocally threaded to threadingly engage the threaded central bore.

In certain embodiments of the invention, the plurality of openings comprise elongate slots having longitudinal axes that are parallel to the longitudinal axis of the body portion of the dental implant in one embodiment, or at any other orientation relative to the longitudinal aspect of the dental implant. In one embodiment, the plurality of openings comprise elongate slots having longitudinal axes that are between about 1 and 179 degrees offset from the longitudinal aspect of the dental implant.

In certain embodiments of the invention, each of the one or more blades have axes that are parallel to the longitudinal axis of the body portion of the dental implant, the blades being of a size configured for passing through the slots created by the opening.

In certain embodiments of the invention, the one or more blades comprises at least two blades that move radially on a common plane.

In certain embodiments of the invention, the at least two blades move outwardly in opposite directions with respect to the body portion of the dental implant.

In certain embodiments of the invention, the at least two blades comprise at least two sets of blades: at least one first set of two blades in a proximal section of the body portion of the dental implant; and at least one second set of two blades in a distal section of the body portion of the dental implant.

In certain embodiments of the invention, the external surface of the body portion of the dental implant is cylindrical and threaded.

In certain embodiments of the invention, in the extended configuration, the blade extending beyond 0.2 mm from the body portion of the dental implant outer surface.

In certain embodiments of the invention, each of the one or more blades includes a flat surface configured to arcuately swivel through each of the slots during extension.

In another embodiment, the invention provides a method for providing support for a dental prosthesis, the method comprising the steps of drilling and/or reaming an opening capable of accommodating a dental implant; inserting a dental implant assembly, the assembly comprising: a dental implant comprising: a body portion located at a distal end of the bladed dental implant; an abutment portion located at a proximal end of the dental implant; a collar portion disposed therebetween; and a central bore extending through the collar portion and into the implant body portion, the central bore having an engagement portion and comprising a plurality of openings radially disposed and extending through the body portion with a plurality of blades pivotally and flexibly connected to the body portion of the dental implant, each blade aligned with one of the plurality of openings; and a shaft member, having an upper portion and a lower portion, said shaft member configured to engage the central bore thereby causing the one or more blades to radially extend from the body portion; and engaging the shaft member, thereby radially extending the blades through the slots and anchoring the dental implant into the bone structure surrounding the implant body portion thus providing support for a dental prosthesis.

These, additional, and/or other aspects and/or advantages of the present invention are: set forth in the detailed description which follows; possibly inferable from the detailed description; and/or learnable by practice of the present invention.

BRIEF DESCRIPTION OF THE DRAWINGS

The present invention will be more readily understood from the detailed description of embodiments thereof made in conjunction with the accompanying drawings of which.

DETAILED DESCRIPTION

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

Figure 1:
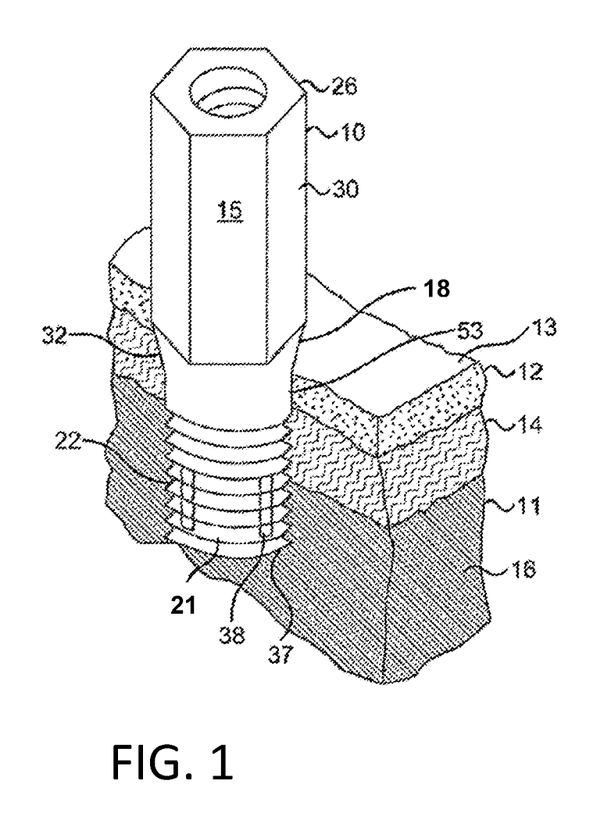
FIG. 1 shows a partially sectioned perspective view of a bladed implant having laterally locking blades in a cross section of bone, according to certain embodiments of the invention.

FIG. 1 depicts an implant assembly 10 with flexible blades in accordance with the present invention referred to by the general reference character 10. In the illustration of FIG. 1, the implant 10 has been placed into a bore 32 formed into bone 11 in a patient's jaw. FIG. 1 depicts alveolar bone section 16 having outer cortical bone portion 14 which terminates at the crest 13 where the soft tissue 12 of a patient's jaw meets the outer cortical bone portion 14. Implant 10 includes a dental implant of a unitary, elongated, hollow, tubular portion 15, having a prosthesis attachment proximal end 26, a collar portion 18 and a body portion 21 of the implant insertion distal end 37. Insertion distal end 37, which is a closed end 25 (FIG. 2), of implant assembly 10 enters furthest into the bore 32, while attachment proximal end 26 of the collar portion 18 provides a site for attaching a dental prosthesis (not shown).

Figure 2:
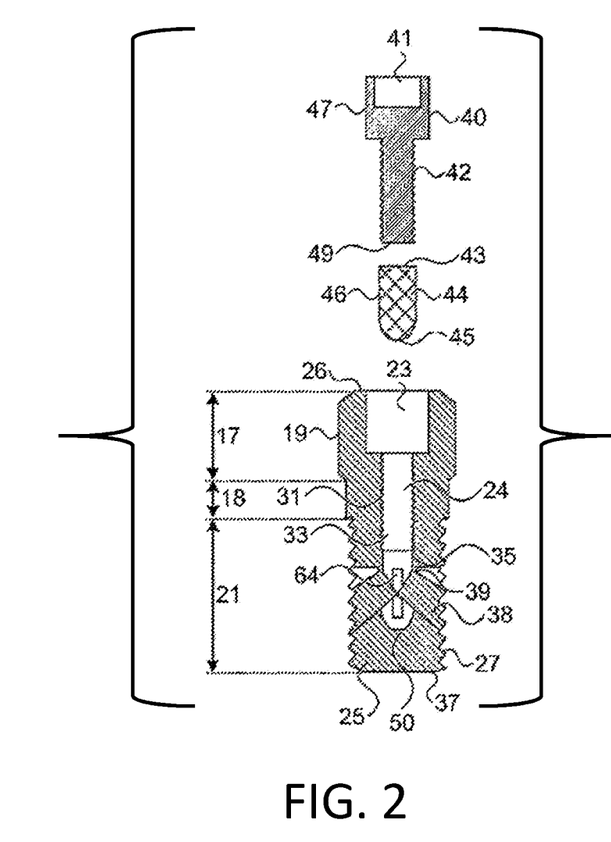
FIG. 2 shows a sectioned elevational exploded view of a bladed implant assembly with a deployment shaft member having an upper portion with an ALLEN™ wrench receptacle, according to certain embodiments of the invention

Referring now to an embodiment shown in FIG. 2, exterior surface of body portion of the dental implant 15 is divided into three sections; an abutment portion 17, a collar portion 18 and a body portion 21. The dental implant 15 includes an interior surface 31 of a central bore 33 and an exterior surface 30. Adjacent to proximal end 26 is an opening 23 with clearance to accommodate insertion of a shaft member 40, operating as a blade actuation means using for example an ALLEN™ screw 40 (see e.g., FIGS. 5, and 12A).

Threads 24 are formed on surface 31 of central bore 33, extending from a base 22 of opening 23 of central bore 33, to a position 35 of central bore 33. The remainder of central bore 33 is unthreaded from position 35 down to an arcuate bottom 50 of central bore 33, with diameter slightly smaller than diameter of threads 24. Threads 27 are also formed on surface 30 of body portion of the dental implant 15 extending the whole length of body portion 21. Threads 27 permit the dental implant 15 to be screwed into bore 32 in bone 11. Abutment portion 17 of the dental implant 15 includes a hexagonal exterior surface 19 to which a hexagonal socket wrench (not shown) may be applied when body portion of the dental implant 15 is being screwed down into bore 32 in bone 11 according to the embodiments of assemblies and methods described herein. In certain other embodiment, the exterior surface 19 is cylindrical, square or any other appropriate shape amenable to manipulation. In one embodiment, collar portion 18 has a diameter that is identical, larger or smaller than the diameter of body portion 21, or abutment portion 17, each a discrete embodiment of the devices provided herein.

Figure 3A:
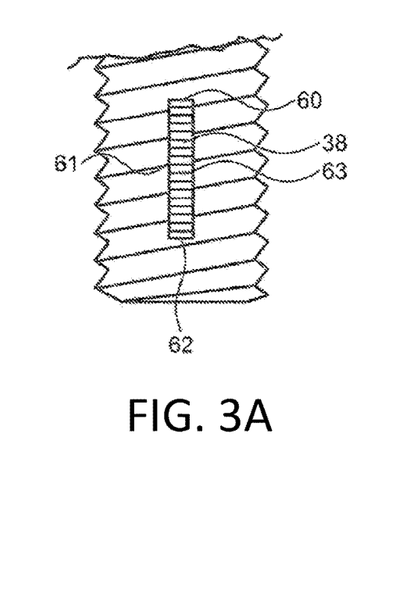
FIG. 3A shows external view of an area near the implant distal insertion end including outer surface of a flexible blade, according to certain embodiments of the invention; 3B shows a cross-section through the two blades, according to certain embodiments of the invention.

In one embodiment (FIG. 3A) of the assemblies and methods described herein, a portion of externally threaded surface 27 of the dental implant 15 contains a plurality of rectangular areas 64 (FIG. 2) spaced around body portion of the dental implant 15 axially; each bounded by three (3) linear slots 61, 62, 63 and a linear groove 60. Slots 61, 62 and 63 pass completely through body portion of the dental implant 15 from surface 30 to surface 31. Groove 60 partially penetrates the metal wall and does not reach surface 31. In other certain embodiments, the plurality of openings 28 comprise elongate slots 64 having longitudinal axes that are between about 1 and 179 degrees offset from the longitudinal aspect of the dental implant 15.

Figure 3B:
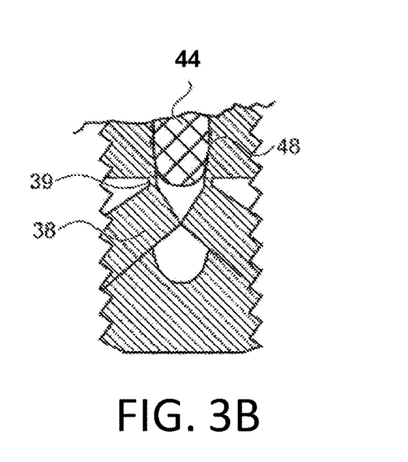

The rectangular surface bounded by slots 61, 62 and 63 and groove 60 form the outer surface of a blade 38 which is flexibly attached to body portion of the dental implant 15 at its upper end 39 (FIG. 3B) and blade 38 may be flexibly pivoted on end 39 to move between retracted and extended position. Blades 38 are optionally a part of the body portion of dental implant 15 and at least partially surrounded by slots 61, 62 and 63. The connection between blades 38 and body portion of the dental implant 15 are flexible and configured to arcuately swivel, at each upper connection 39 radially outwards to a fully extended position as in FIG. 5.

Implant 10 also includes shaft member 40, illustrated in FIG. 2. Shaft member 40 includes an upper portion 41 defining an internal socket adapted to receive a hexagonal, triangular, elliptical or square wrench (not shown). Threads 42 of shaft member 40 are formed to mate with and engage threads 24 formed on surface 31 of dental implant 15. Shaft member 40 also includes a detachable lower actuating portion 44 with flat surface 43 at the proximal end, and an arcuate tip surface at the distal end 45 of detachable actuating lower portion 44. An outer smooth surface 48 of detachable actuating lower portion 44 is cylindrical, enabling it to slide on inner surface 31 of body portion of dental implant 15 below point 35 when actuated by the advance of the upper portion of shaft member 40 into the body portion of dental implant 15.

Accordingly and in one embodiment, provided herein is a bladed dental implant assembly 10 for supporting a dental prosthesis, the assembly comprising: a dental implant 15 comprising: a body portion 21 located at a distal end of the bladed dental implant 15; a abutment portion 17 located at a proximal end 26 of the dental implant 15; and a central bore 33 extending through the abutment portion 17 and into the implant body portion 21, the central bore 33 having an engagement portion 24 and comprising a plurality of openings 61, 62 and 63, radially disposed and extending through the body portion 21 with a plurality of blades 38 flexibly attached to the body portion 21 of the dental implant 15, each blade 38 aligned with one of the plurality of openings and capable of moving between a retracted position to an extended position; and a shaft member 40 comprising an upper portion 42 and a detachable actuating lower portion 44, said shaft member configured to engage the central bore 33 thereby causing the actuating lower portion 44 to radially extend the blades 38 from the body portion 21, anchoring the dental implant assembly 10 into the bone structure surrounding the implant body portion 21. In certain embodiments, a collar portion 18 is disposed between abutment portion 17 and body portion 21, such that each portion comprising implant 15, is detachable and adapted to be connected to each other portion.

Rotation of shaft member 40 within body portion of dental implant 15 causes detachable actuating lower portion 44 to force blades 38 to extend radially, flexibly pivoting, also referred to as swiveling as noted above, at point 39, and extend into bone 11.

As suggested by FIG. 2, arcuate distal end 45 of detachable actuating lower portion 44 is inserted into the body portion of dental implant 15 at end 26 thereof and detachable actuating lower portion 44 slides into position, making contact with surface 48 of the non-threaded portion of central bore 33 of dental implant 15, shaft member 40 is inserted into dental implant 15 at end 26 thereof and threads 42 of shaft member 40 mate with threads 24 formed on surface 31 of the body portion of dental implant 15.

Rotation of shaft member 40 into the dental implant 15 advances shaft member 40 along the body portion of dental implant 15 from proximal end 26 towards distal end 37. In certain embodiments the insertion of the dental implant 15, into the bone 11, is carried out by rotating the implant 15 using a wrench that is complementary to either the outer surface of the abutment 17, or internal surface defined by opening 23 (see e.g., FIG. 2).

After dental implant 15 has been screwed into bore 32, shaft member 40 is rotated within dental implant 15 to advance shaft member 40 towards distal end 37 of the body portion of dental implant 15 until a tip 49 of shaft member 40 contacts with an upper surface 43 of detachable actuating lower portion 44 and begins to move detachable actuating lower portion 44 towards central bore 33, inside dental implant 15.

Figure 4:
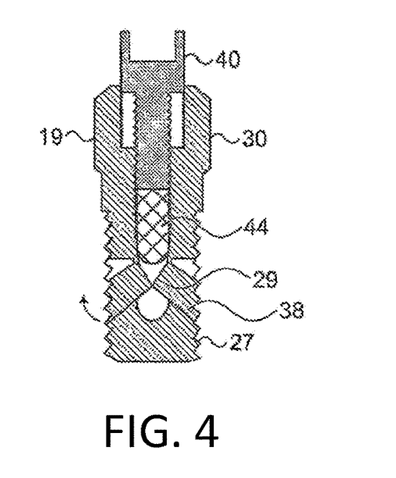
FIG. 4 shows a cross-section through the implant assembly with partially engaged shaft member, according to certain embodiments of the invention.

Referring now to an embodiment of the dental implant assembly shown in FIG. 4, as advance of screw 42 forces detachable actuating lower portion 44 towards bottom 50, blade 38 swivels radially outwards (FIG. 5) pivoting on upper corner 39 (FIG. 3B), thereby extending outwards and penetrating into bone 11.

Figure 5:
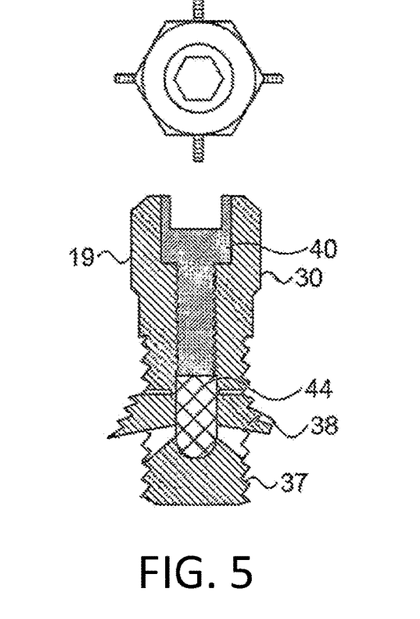
FIG. 5 shows a cross-section through the implant assembly with fully engaged shaft member and extended blades, according to certain embodiments of the invention.

FIG. 5 shows an embodiment of the dental implant assembly, wherein blades 38 in their fully extended position are protruding radially outwards through slots 61, 62 and 63, penetrating into bone 11, after shaft member 40 has been advanced as far as shaft member 40 can advance towards insertion end 37, so that surface 45 of detachable actuating lower portion 44 reaches a position as close as possible to bottom 50 of central bore 33. Blades 38 are now locked in the extended position by detachable actuating lower portion 44.

In certain embodiments, after implant assembly 10 has been properly secured in bone 11, a dental prosthesis (not shown) is typically attached to implant 10 by means of cement in one embodiment (not shown), or, other connectors, for example a screw in other discrete embodiments of the assemblies and methods described herein.

A portion of the prosthesis immediately adjacent to end 26 of the abutment portion 17 of dental implant 15 is a healing cap (not shown) with an internal hexagon which is adapted to fit over and envelopes hexagonal portion 19 of surface 30 at proximal end 26 of dental implant 15, to create a smooth outer surface of combined implant assembly 10 and prosthesis. The distal portion of the prosthesis may be a single tooth in one embodiment, or an abutment for a multi-tooth bridge, a support for an over denture superstructure, a support for a fixed or detachable prosthesis, or in some instances an anchorage for an orthodontic retraction mechanism in other discrete embodiments of the assemblies and methods described herein.

In certain embodiments, dental implant 15, detachable actuating lower portion 44 and the upper portion of shaft member 40 are optionally made from a titanium alloy or noble metal alloy. In certain embodiments, threads 27 on surface 30 of the body portion of dental implant 15 are optionally 3.3 mm minimum diameter metric thread, and the unthreaded portion of surface 30 optionally has a hexagonal dimension of 3.3 mm AF minimum; measured across the flats.

In certain embodiments, dental implant 15 is fabricated to have various different lengths $L_B$, optionally in the range of between about 4 mm to 17 mm, from distal insertion end 37 of dental implant 15 to proximal end 26 thereof and through collar portion 18. In other embodiments, the dental implant 15 is fabricated to have lengths $L_B$, optionally in the range of between about 5 mm to 15 mm, or optionally in the range of between about 10 mm to 17 mm, or optionally in the range of between about 4 mm to 10 mm, or optionally in the range of between about 4 mm to 8 mm, or optionally in the range of between about 8 mm to 12 mm, or optionally in the range of between about 12 mm to 16 mm, or optionally in the range of between about 12 mm to 17 mm, in other discrete embodiments of the assemblies described herein, which in certain other embodiments are used in the methods provided herein. It is to be understood that the devices provided herein could be used as implants for orthopedic applications upon reconfiguration of the various dimensions and materials used in the components described herein.

In certain embodiments, a 1.2 mm diameter metric thread is optionally used for threads 24 and 42 formed respectively on surface 31 of dental implant 15 and on outer surface 47 of the upper portion of shaft member 40.

In certain embodiments of the assemblies described herein, the rotation angle of blades 38 flexibly attached to the body portion 21 of dental implant 15; on completion of actuation is optionally between about 20° and 90°, giving a circumscribed circumferential circle fully actuated of about 1 millimeter or greater than the diameter of screw thread 27 on exterior surface 30 of the body portion 21 of dental implant 15.

The portion of central bore 33 closer to distal end 37 than point 39 of the body portion 21 of dental implant 15 has an internal diameter the same or somewhat less than that of screw thread 24, allowing detachable actuating lower portion 44 to be easily inserted to take up its initial position touching surface 29 of blades 38.

In certain embodiments of the assemblies described herein, detachable actuating lower portion 44 diameter is less than that of the portion of internal drilled central bore 33 closer to bottom 50 than point 39 of the body portion 21 of dental implant 15, in order to permit axial sliding movement of detachable actuating lower portion 44 inside the portion of drilled central bore 33 closer to bottom 50 than point 39 of the body portion 21 of dental implant 15.

Figure 7A:
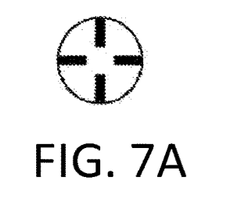
FIG. 7 shows a possible alignment of first row of blades (a) compared to two possible alignments of second row of blades (b and c), according to certain embodiments of the invention.
Figure 7B:
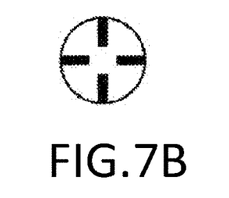
Figure 7C:
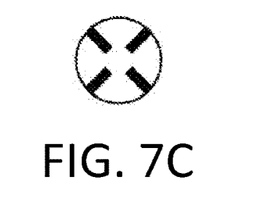

In certain embodiments shown in FIG. 7 of the assemblies described herein, there are optionally four surfaces 64 (FIG. 2) of blades 38 spaced uniformly about the circumference in the body portion 21 of dental implant 15, wherein two sets of two blades 38 each are disposed longitudinally in the body portion 21 of the dental implant 15, such that one set is closer to distal end 37. FIG. 7 shows embodiments of the possible spatial relationship between the two sets of blades according to the invention.

In certain embodiments of the assemblies described herein, five surfaces 64 of blades 38, optionally may be uniformly spaced about the circumference in the portion of internal drilled central bore 33 closer to insertion end 37 than point 39 of the body portion 21 of dental implant 15.

In certain embodiments of the assemblies described herein, exterior surface 30 of dental implant 15 close to attachment proximal end 26 optionally has a hexagonal 19 section. This may have a partially or completely circular section in place of hexagonal surface 19.

In certain embodiments of the assemblies described herein, there are optionally four (4) blades 38. However, in other embodiments, the number of blades may optionally be any number from one and more blades 38. In alternative embodiments two, or four, six or even eight or even more blades in other discrete embodiments of the assemblies described herein are optionally placed on the circumference of the body portion 21 of dental implant 15.

Figure 6:
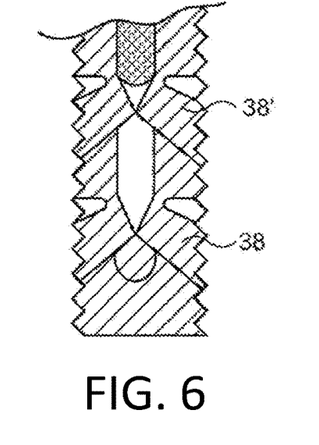
FIG. 6 shows a cross-section of the body portion having two rows of blades, according to certain embodiments of the invention.

An alternative embodiment of the assemblies provided herein, which, in certain embodiments are used in the methods described herein, is shown in FIG. 6, wherein there is an extra row of flexible blades 38. Optionally body portion 21 of dental implant 15 has a much longer threaded collar portion 18 (FIG. 10) with an exterior surface 27 that can accommodate an extra row of blades. Actuation of blades 38 is in a similar manner to that of a single row of blades 38. As shown in top views in FIG. 7, blades 38 may or may not be aligned with circumferential position of blades 38.

Figure 8:
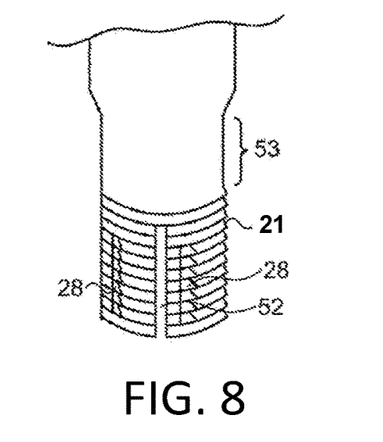
FIG. 8 shows a perspective view of the body portion of the dental implant with axial groove between two blades, according to certain embodiments of the invention.

In certain embodiments of the assemblies described herein, shown in FIG. 8, shallow longitudinal grooves 52, less than the length of section 21, may be included in screw threaded surface 27. Grooves 52 may be placed parallel to and between longitudinal blade slots 28 on surface 30 of the body portion 21 of dental implant 15. The number of grooves 52 is dependent on the number of blades 38.

In certain embodiments of the assemblies described herein, external surface 30 of the body portion 21 of dental implant 15, close to insertion distal end 37 has a threaded surface 27. In certain other embodiments, threaded surface 27 may be smooth without screw thread. In certain embodiments, the smooth surface may also be roughened by special mechanical or chemical treatment or in other embodiments coated with a porous mineral in one embodiment, or ceramic coating, or Platelet-derived growth factor-BB (PDGF-B), or stromal bone marrow cells, or mesenchymal stem cells, in order to encourage accelerated bone growth. Additional medication in the form of controlled or sustained release coating may also be employed.

In certain embodiments of the assemblies 10 described herein, part of surface 30 of the collar portion 18 of dental implant 15, has a smooth section 53 in one embodiment or a rough surface in other embodiments of the surface 53 of collar 18. Surface 53 may become continuous to threaded surface 27, and in addition, threaded surface 27 may become identical with smooth surface 53. Due to the fact that the design of the implant, after blade actuation, produces a distal increase in implant cross-section (and thus lowering its centre of gravity), the force moment on the implant moves towards the distal end, farther from the collar 17 of the implant 15 and away from the ridge of the edentulous residual bone/crest. In such a manner, bone resorption is reduced and may be eliminated. Likewise, the creation of a smooth surface between the abutment portion 17 and the collar portion 18, eliminates crevices that may provide location for the growth of bacterial leading to periodontic gum disease.

In certain embodiments of the assemblies described herein, all internal surfaces are uncoated. In alternative embodiments some or all internal surfaces 31 are optionally partially or completely coated by a coating of gold, gold alloy or other noble metal or alloy.

In certain embodiments of the assemblies described herein, surfaces of detachable actuating lower portion 44 are uncoated. In alternative embodiments, the outer surfaces of detachable actuating lower portion 44, blade and ALLEN™ actuated shaft member 40 may be partially or completely coated by a coating of gold, gold alloy or other noble metal or alloy.

Figure 9:
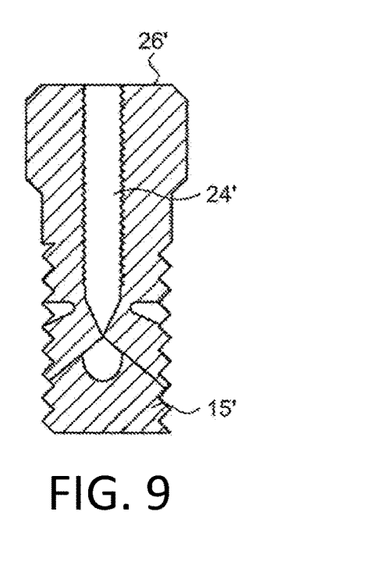
FIG. 9 shows a cross-sectional view of the body portion of the dental implant having a screw thread extending therethrough, according to certain embodiments of the invention.

In certain embodiments of the assemblies described herein, the upper portion of shaft member 40 is be replaced by a Philips head or Philips headless screw (not shown). FIG. 9 shows an embodiment in which an interior screw thread 24' of the body portion 21 of dental implant 15' extends to attachment end 26' of the body portion 21 of dental implant 15'.

Figure 10:
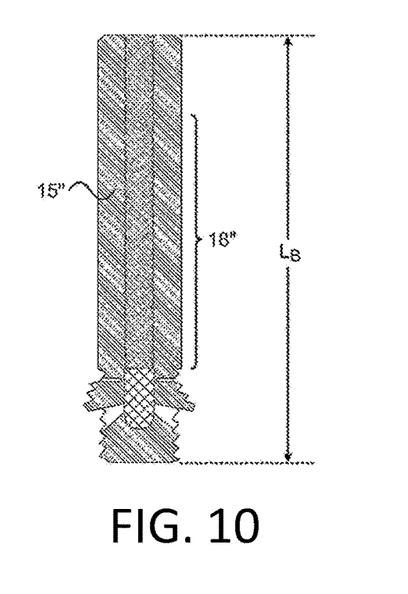
FIG. 10 shows a cross-sectional view of the body portion of the dental implant with an extended distal section, according to certain embodiments of the invention.

In certain embodiments of the assemblies described herein of the body portion 21 of dental implant 15", shown in FIG. 10, the length of collar 18" is extended to provide an overall length $L_B$ of the body portion 21 of dental implant 15", in order to avoid using a separate abutment, where it would normally be necessary. In one embodiment, dental implant 15, comprises discrete and detachable components, wherein the discrete components are a body portion 21, a collar portion 18 and an abutment portion 17 all adapted to be connected to each other. Any embodiment directed to a component of the body portion 21 the collar portion 18 and the abutment portion 17 covers the discrete and detachable components and is within the scope of the invention.

Figure 11:
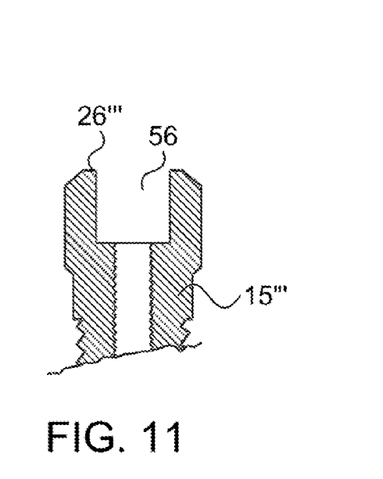
FIG. 11 shows a cross-sectional view of a collar portion of the dental implant including an internal hexagon for attachment of an abutment, according to certain embodiments of the invention.

In certain embodiments of the assemblies described herein shown in FIG. 11, attachment end 26''' of the body portion 21 of dental implant 15''' may have an internal hexagonal, triangular, square or elliptical section 56, in order to facilitate attachment of abutment 17.

Figures 12A, 12B, 12C:
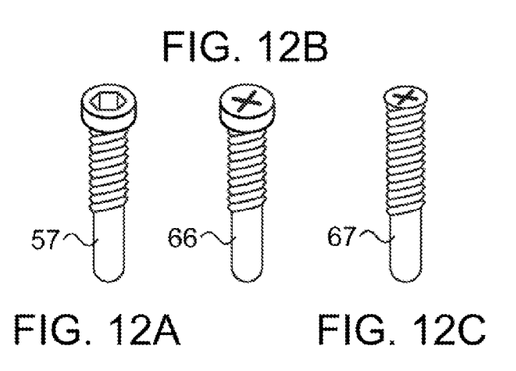
FIGS. 12A, 12B and 12C show a shaft member with ALLEN™ (12A) wrench, PHILIPS™ head (12B), and PHILIPS™ headless receptacles (12C), according to certain embodiments of the invention.

In a still further embodiment upper portion shaft member 40 and detachable actuating lower portion 44 are combined into a single special blade actuation ALLEN™ screw 57 shown in FIG. 12A or a special blade actuation headed PHILIPS™ 66 or headless PHILIPS™ screw 67, shown respectively in FIGS. 12B and 12C. In certain embodiments shaft member 40 is a single member wherein portions 57, 66 and 67 respectively are continuous and are threaded.

Figure 13:
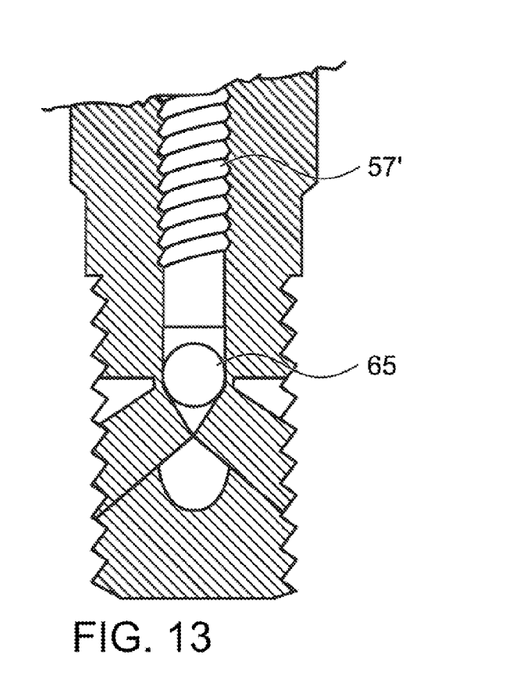
FIG. 13 shows a ball configured to transfer axial force to the blades, according to certain embodiments of the invention.

In certain embodiments of the assemblies described herein shown in FIG. 13, a ball 65, is utilized to transfer advancing force of screw 57' to actuate blades 38; using, for example, an ALLEN™ screw, or PHILIPS™ head screw driver.

In further embodiments, detachable actuating lower portion 44 has a cylindrical surface 46.

Figure 14:
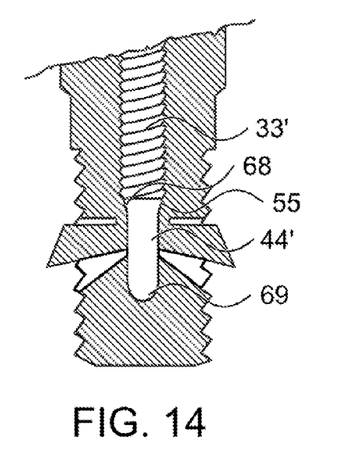
FIG. 14 shows a cross-sectional view of the body portion of the dental implant with a shaft member fully engaged and blades in their axially locked position, according to certain embodiments of the invention.

An embodiment shown in FIG. 14, wherein detachable actuating lower portion 44' having a partial or completely tapered smooth surface 68. The body portion 21 of dental implant 15 includes an interior central bore 33' with a tapered surface 55 to provide seating of terminal end 69 of surface 68 of detachable actuating lower portion 44' on surface 55 of central bore 33'.

Figure 15A:
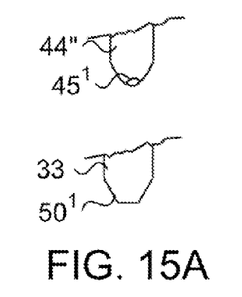
FIG. 15 shows some of the potential shapes of and interior hole bottom and lower surface of the shaft member, according to certain embodiments of the invention.
Figure 15B:
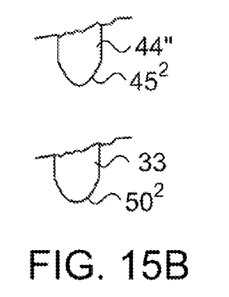

In certain embodiments of the assemblies described herein, surface 45 of detachable actuating lower portion 44 and bottom distal end 50 of drilled central bore 33 have the same arcuate shape. Further, a surface $45^1$ or $45^2$ of detachable actuating lower portion 44" and a bottom distal end $50^1$ of a central bore 33' or a bottom distal end $50^2$ of central bore 33' optionally have shapes shown by FIGS. 15A and 15B respectively.

In certain embodiments of the assemblies described herein, outer surface 64 of blade 38 is optionally be trapezoidal in profile, with groove 60 being somewhat longer than slot 62.

In certain embodiments of the assemblies described herein, the cross-sectional and axial dimensions of dental implant 15 may be increased as is necessary to suit a patient's bone or jaw bone.

In certain embodiments, the assemblies described herein are used in the methods provided herein. Accordingly and in one embodiment, provided herein is a method of providing support for a dental prosthesis, the method comprising the steps of: drilling and/or reaming an opening capable of accommodating a dental implant; inserting a dental implant assembly 10, the assembly comprising: a dental implant 15 comprising: a body portion 21 located at a distal end of the bladed dental implant 15; an abutment portion 17 located at a proximal end 26 of the dental implant 15; and a central bore 33 extending through the abutment portion 17 and into the implant body portion 21, the central bore 33 having an engagement portion 31 and comprising a plurality of openings 28 radially disposed and extending through the body portion 21 with a plurality of blades 38 flexibly attached to the body portion 21 of the dental implant 15, each blade aligned with one of the plurality of openings 28; and a shaft member 40, comprising: an upper portion 42; and a detachable actuating lower portion 44, said shaft member configured to engage the central bore 33 thereby causing the plurality of blades 38 to radially extend from the body portion 21; and engaging the shaft member 40, thereby causing the actuating lower portion 44 to radially extend the blades 38 through the slots 28 and anchoring the dental implant 10 into the bone structure 11 surrounding the implant body portion 21 thus providing support for a dental prosthesis.

The inventors have discovered that the above noted expanding dental implants, exemplified by U.S. Pat. No. 6,332,778 (Choung), create stress during expansion, such that the deformable expanding portions may shatter the adjacent bone. In addition to prohibiting implantation, a shattered bone may require multiple bone-regenerative surgical procedures.

In distinct contrast, the present invention does not create substantial compressive forces during extension of the blades, thereby possibly averting the problem of damaging adjacent bone.

The inventors have additionally, discovered that in the event that should the expanding dental implants, exemplified by U.S. Pat. No. 6,332,778 (Choung), require removal, it is often necessary to utilize a trephine having sufficient diameter to surround the deformed implant ends.

The result of trephine removal is a cylindrical bone core that leaves a bone defect that may be recalcitrant to implant replacement.

In distinct contrast, using the implant 15 wherein the body portion 21, the collar portion 18 and the abutment portion 17 are discrete and detachable, one could remove the collar 18 leaving the undamaged body portion 21, thereby averting the necessity of creating a large defect using a trephine as in Choung.

Of course, the present invention is not intended to be restricted to any particular form or arrangement, or any specific embodiment disclosed in this document, or any specific use, since the same may be modified in various particulars or relations without departing from the spirit or scope of the claimed invention as shown above and described of which the assembly shown is intended only for illustration and for disclosure of an operative embodiment and not to show all of the various forms or modifications in which the present invention might be embodied or operated.

In the above description, an embodiment is but an example or implementation of the inventions. The various appearances of phrases like "one embodiment", "an embodiment", or "certain embodiments of the assemblies described herein", do not necessarily all refer to the same embodiments.

Although various features of the invention may be described in the context of a single embodiment, the features may also be provided separately or in any suitable combination. Conversely, although the invention may be described herein in the context of separate embodiments for clarity, the invention may also be implemented in a single embodiment.

Reference in the specification to "certain embodiments of the assemblies described herein", "an embodiment", "one embodiment", or "other embodiments" means that a particular feature, structure, or characteristic described in connection with the embodiments is included in at least certain embodiments of the assemblies described herein, but not necessarily all embodiments, of the inventions.

It is to be understood that the phraseology and terminology employed herein is not to be construed as limiting and are for descriptive purpose only.

The principles and uses of the teachings of the present invention may be better understood with reference to the accompanying description, figures, and examples.

It is to be understood that the details set forth herein do not construe a limitation to an application of the invention.

Furthermore, it is to be understood that the invention can be carried out or practiced in various ways and that the invention can be implemented in embodiments other than the ones outlined in the description above.

It is to be understood that the terms "including", "comprising", "consisting", and grammatical variants thereof do not preclude the addition of one or more components, features, steps, or integers or groups thereof and that the terms are to be construed as specifying components, features, steps, or integers.

If the specification or claims refer to "an additional" element, that does not preclude there being more than one of the additional element.

It is to be understood that where the claims or specification refer to "a" or "an" element, such reference is not be construed that there is only one of that element.

It is to be understood that where the specification states that a component, feature, structure, or characteristic "may", "might", "can", or "could" be included, that particular component, feature, structure, or characteristic is not required to be included.

Where applicable, although state diagrams, flow diagrams or both may be used to describe embodiments, the invention is not limited to those diagrams or to the corresponding descriptions. For example, flow need not move through each illustrated box or state, or in exactly the same order as illustrated and described.

Methods of the present invention may be implemented by performing or completing manually, automatically, or a combination thereof, selected steps or tasks.

The term "method" may refer to manners, means, techniques, and procedures for accomplishing a given task including, but not limited to, those manners, means, techniques, and procedures either known to, or readily developed from known manners, means, techniques, and procedures by practitioners of the art to which the invention belongs.

The descriptions, examples, methods, and materials presented in the claims and the specification are not to be construed as limiting, but rather as illustrative only.

Meanings of technical and scientific terms used herein are to be commonly understood as by one of ordinary skill in the art to which the invention belongs, unless otherwise defined.

The present invention may be implemented in the testing or practice with methods and materials equivalent or similar to those described herein.

Any publications, including patents, patent applications and articles, referenced or mentioned in this specification are herein incorporated in their entirety into the specification, to the same extent as if each individual publication was specifically and individually indicated to be incorporated herein. In addition, citation or identification of any reference in the description of certain embodiments of the assemblies described herein shall not be construed as an admission that such reference is available as prior art to the present invention.

While the invention has been described with respect to a limited number of embodiments, these should not be construed as limitations on the scope of the invention, but rather as exemplifications of some of the preferred embodiments. Other possible variations, modifications, and applications are also within the scope of the invention. Accordingly, the scope of the invention should not be limited by what has thus far been described, but by the appended claims and their legal equivalents.

What is claimed is:

1. A bladed implant assembly for supporting a prosthesis, the assembly comprising:
   a. a unitary implant comprising:
      i. a body portion located at a distal end of the unitary implant, wherein an external surface of the body portion is threaded;
      ii. an abutment portion located at a proximal end of the unitary implant;
      iii. a collar portion disposed therebetween; and
      iv. a central bore extending through the abutment portion and into the unitary implant body portion having a distal end, the central bore having an engagement portion and comprising one or more openings radially disposed and extending through the body portion with one or more blades flexibly attached to the body portion of the unitary implant, each blade being a portion of the external surface of the body portion, aligned with one or more of the openings and capable of moving between a retracted position and an extended position, wherein, in the retracted position, the external surface of the one or more blades is threaded in a form continuous with the threaded external surface of the body; and
   b. a shaft member comprising:
      i. an upper portion; and
      ii. a detachable actuating lower portion, wherein the actuating lower portion includes a proximal end having a flat surface and a distal end having arcuate surface, corresponding to an arcuate surface of the distal end of the central bore, said shaft member configured to engage the central bore thereby causing the actuating lower portion to radially extend the one or more blades from the body portion, anchoring the unitary implant into the bone structure surrounding the implant body portion.

2. The assembly according to claim 1, wherein the engagement portion of the central bore is threaded and the shaft member is reciprocally threaded to threadingly engage the threaded central bore.

3. The assembly according to claim 1, wherein the one or more openings define substantially elongate slots, that are axially parallel to the body portion of the unitary implant.

4. The assembly according to claim 1, wherein each of the one or more blades are configured to arcuately swivel during extension.

5. The assembly according to claim 4, wherein the one or more blades comprise at least two blades that extend radially on a common plane.

6. The assembly according to claim 5, wherein the at least two blades extend radially at an angle of about 180° with respect to each other.

7. The assembly according to claim 6, comprising at least two sets of blades, a first set disposed at a proximal section of the body portion and at least a second set disposed at a distal section of the body portion.

8. The assembly according to claim 1, wherein upon engagement of the actuating portion of the shaft member, the one or more blades radially extend to a position of no less than 0.2 millimeter from the external surface of the body portion.

9. A method providing support for a prosthesis, the method comprising the steps of:
   a. drilling and/or reaming an opening capable of accommodating an implant;
   b. inserting an implant assembly, the assembly comprising:
      i. a unitary dental implant comprising:
         1. a body portion located at a distal end of the unitary dental implant, wherein an external surface of the body portion is threaded;
         2. an abutment portion located at a proximal end of the unitary dental implant;
         3. a collar portion disposed therebetween; and
         4. a central bore extending through the abutment and collar portion and into the unitary implant body portion having a distal end, the central bore having an engagement portion and comprising at least one opening radially disposed and extending through the body portion with at least one blade flexibly attached to the body portion of the unitary implant, each blade being a portion of the external surface of the body portion, aligned with one of the one or more openings, capable of moving between a retracted position and an extended position, wherein, in the retracted position, the external surface of the blade is threaded in a form continuous with the threaded external surface of the body; and
      ii. a shaft member, comprising:
         1. an upper portion; and
         2. a detachable actuating lower portion wherein the actuating lower portion includes a proximal end having a flat surface and a distal end having arcuate surface, corresponding to an arcuate surface of the distal end of the central bore, said shaft member configured to engage the central bore thereby causing the at least one blade to radially extend from the unitary body portion; and
   c. engaging the shaft member, thereby causing the actuating lower portion to radially extend the at least one blade through the at least one opening and anchoring the unitary implant into the bone structure surrounding the implant body portion thus providing support for a dental prosthesis.

10. The method of claim 9, whereby an external surface of the body portion in the implant of the assembly is threaded.

11. The method of claim 10, whereby the step of inserting the implant assembly comprises screwing the implant into the opening.

12. The method of claim 9, further comprising the step of removing the upper portion of the detachable shaft member.

* * * * *